United States Patent [19]

Mizoule

[11] 4,370,338

[45] Jan. 25, 1983

[54] MEDICAMENT BASED ON 2-AMINO-6-TRIFLUOROMETHOXY-BENZOTHIAZOLE

[75] Inventor: Jacques Mizoule, Villeneuve la Garenne, France

[73] Assignee: Pharmindustrie, Gennevilliers, France

[21] Appl. No.: 308,695

[22] Filed: Oct. 5, 1981

[30] Foreign Application Priority Data

Oct. 17, 1980 [FR] France ................ 80 22218

[51] Int. Cl.³ ............................................ A61K 31/425
[52] U.S. Cl. .................................................... 424/270
[58] Field of Search ................. 424/270; 548/152, 164

[56] References Cited

U.S. PATENT DOCUMENTS 3,876,653 4/1975 Kasuya et al. ............... 424/270 X
3,879,531 4/1975 Ariyan et al. ................... 424/270

OTHER PUBLICATIONS

Yagupol'skii et al., Chemical Abstracts, vol. 60, 692(a), 1964.

*Primary Examiner*—Albert T. Meyers
*Assistant Examiner*—J. W. Rollins, Jr.
*Attorney, Agent, or Firm*—Beveridge, DeGrandi and Kline

[57] ABSTRACT

Anticonvulsant, anxiolytic and hypnotic medicament containing, as active substance, 2-amino-6-trifluoromethoxy-benzothiazole or a salt of this compound with a pharmaceutically acceptable acid.

7 Claims, No Drawings

MEDICAMENT BASED ON 2-AMINO-6-TRIFLUOROMETHOXY-BENZOTHIAZOLE

The present invention relates to a new medicament, particularly useful as an anticonvulsant, anxiolytic and hypnotic, which contains as the active ingredient 2-amino-6-trifluoromethoxybenzothiazole or a salt of this compound with a pharmaceutically acceptable acid.

2-Amino-6-trifluoromethoxy-benzothiazole, of the formula:

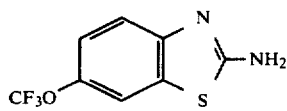

is a known compound, which may be prepared by the action of potassium thiocyanate and bromine on 4-trifluoromethoxy-aniline in acetic acid medium (cf. Chemical Abstracts 60, 692, 1964; and L. M. YAGUPOL'-SKII, L. Z. GANDEL'SMAN, Zh. Obshch. Khim. 33, 2301, 1963). A method of operation which can be used for this preparation is as follows:

A solution of 77 g of bromine in 220 ml of acetic acid is added drop by drop, in a period of one hour, to a solution of 84 g of 4-trifluoromethoxy-aniline and 187 g of potassium thiocyanate in 500 ml of acetic acid. The mixture is stirred overnight at the ambient temperature. The reaction mixture is then poured into 2 liters of water. The resulting mixture is cooled in an icebath and neutralized by addition of ammonia. The insoluble material is separated by filtration, washed with water, then recrystallized in an ethanol-water mixture (50—50). 77 g of 2-amino-6-trifluoromethoxy-benzothiazole, which melts at 119° C., are thus obtained.

Nevertheless, even if the 2-amino-6-trifluoromethoxybenzothiazole is a known compound, no pharmacological property or therapeutic application has been described for this compound up to the present.

It has now been found, according to the present invention, that this compound possesses remarkable pharmacological properties which enable it to be used as an active ingredient of medicaments.

PHARMACOLOGICAL PROPERTIES (1) anticonvulsant activity

In spite of its chemical structure, which is very different from that of the benzodiazepines, 2-amino-6-trifluoromethoxybenzothiazole acts like these on the gabaergical mechanisms which control a certain number of psychomotric reactions of central origin. This is illustrated by the fact that this compound inhibits convulsions caused in an animal by an inhibitor of the GABA synthesis (GABA = α-aminobutyric acid) such as isoniazide (INH), and this at doses 4 times less than those which are necessary to inhibit convulsions caused by blockage of the central receptor sites of the glycine by strychnine. This is not the case with other non-benzodiazepinic anticonvulsant agents such as zoxazolamine, the action of which on convulsions caused by INH or by strychnine is practically the same.

These effects have been shown in vivo on the mouse and the rat. In the case of the mouse, the product is administered orally, in increasing doses, to batches of 10 male mice CD1 (Charles River) of 20–27 g, 90 minutes before exposure to a supramaximal electric shock (ESM), according to the method described by G. M. Everett and R. K. Richards (J. Pharmacol, Exptl. Therap. 81, 402, 1944). The results are expressed in the form of a 50% effective dose ($ED_{50}$), which is the dose of product protecting 50% of the animals against the convulsions caused by the ESM.

In the case of the male rat CD (Charles River) of 200–230 g, the convulsions are caused by the subcutaneous injection either of 500 mg/kg of isoniazide (INH) or of 1.5 mg/kg of a strychnine in the form of the sulfate. According to the protocol described by J. L. Costa et al. (Adv. Biochem., Pharmacol., 14, 113, 1975), the product to be tested is administered intraperitoneally 25 minutes after the isoniazide and 5 minutes before the strychnine. The number of animals having shown convulsions is registered during an observation period of 60 minutes after the injection of the isoniazide and 25 minutes after the injection of the strychnine.

In each case of $ED_{50}$ (dose of product protecting 50% of the animals against the convulsions) is determined. The results obtained are collected in the following Table 1, wherein there are also given, for comparison, the results provided by two reference anticonvulsants (valproic acid, phenobarbital).

TABLE 1

| | $ED_{50}$ (mg/kg) | | |
|---|---|---|---|
| Products | E.S.M. (mouse orally) | I.N.H. (rat ip) | Strychnine (rat ip) |
| 2-Amino-6-trifluoro-methoxy-benzothiazole | 10 | 2.2 | 8.4 |
| Valproic acid | 450 | 180 | inactive at 600 |
| Phenobarbital | 26 | 16 | 33 |

(2) Anxiolytic activity

The anxiolytic activity of the product has been shown on the mouse, by use of the method called the test of the 4 plates, described by J. R. Boissier et al. (Europ. J. Pharmacol., 4, 145, 1968).

90 minutes after oral administration of the product, the animal undergoing the test (male mouse CD1 Charles River of 20–27 g) is placed in a box the base or floor of which is formed of four separated metal plates. Each time the animal passes from one plate to another, all the plates are electrified. The animal rapidly associates displacement and an electric shock and stays immovable on one of the plates. The number of crossings effected by the mouse in 2 minutes is thus determined.

The animals are divided into groups of 20 mice, the control group receiving only the vehicle. The results obtained for the treated groups are expressed by a percentage increase of the number of passages with respect to the control group and are collected in Table 2 below.

TABLE 2

| Dose of 2-amino-6-trifluoro-methoxy-benzothiazole in mg/kg, taken orally | % increase of the number of passages |
|---|---|
| 5 | +50 |
| 10 | +61 |
| 20 | +100 |
| 25 | +162 |
| 25 | +215 |

Toxicological properties

The acute toxicities of the 2-amino-6-trifluoromethoxybenzothiazole have been determined on the male mouse CD1 (Charles River) by intraperitoneal and oral methods. The $LD_{50}$ has been calculated, after 3 days observation, by the cumulative method of J. J. Reed and H. Muench (Amer. J. Hyg., 27, 493, 1938). The $LD_{50}$ obtained are collected in the following Table 3.

TABLE 3

| Method of administration | $LD_{50}$ mg/kg |
|---|---|
| Intraperitoneal | 46 |
| Oral | 67 |

Therapeutic use

The medicament according to the invention, which contains 2-amino-6-trifluoromethoxy-benzothiazole or a salt of this compound with a pharmaceutically acceptable acid associated with a pharmaceutically acceptable vehicle, can be used in human therapy as an anticonvulsant, anxiolytic and hypnotic. Suitable pharmaceutically acceptable acids include hydrochloric, hydrobromic, sulfuric, nitric, phosphoric, methanesulfonic, ethane disulfonic acids and suitable pharmaceutically acceptable vehicles include water, saline, vegetable oils such as olive oil, sesame oil, and alcohols such as ethanol, propylene glycol. The medicament may be presented in all the forms in use in the field of medicaments, such as compressed tablets, capsules, gelatin-coated pills, suppositories, ingestable or injectable solutions or suspensions, etc.

The dosage depends on the effects sought and on the method of administration used. For example, taken orally, it may be from 5 to 250 mg of active substance per day, with unitary doses ranging from 1 to 50 mg of active substance.

The recipes set forth hereafter for the medicament according to the invention are given as examples and are not limitative.

Recipes in the form of compressed tablets a. Composition: The compositions of recipes A, B and C are as follows:

|  | A | B | C |
|---|---|---|---|
| 2-Amino-6-trifluoromethoxy-benzothiazole (active substance) | 10 mg | 25 mg | 50 mg |
| Microcrystalline cellulose | 20 mg | 75 mg | 75 mg |
| Mannitol | 50 mg | 41 mg | 41 mg |
| Polyvidone | 4 mg | 10 mg | 10 mg |
| Methylated casein | 10 mg | 0 | 0 |
| Carboxymethylstarch (sodium salt) | 0 | 25 mg | 25 mg |
| Colloidal silica | 0 | 4 mg | 4 mg |
| Talc | 5 mg | 18 mg | 18 mg |
| Magnesium stearate | 1 mg | 2 mg | 2 mg |
| Total for one compressed tablet | 100 mg | 200 mg | 225 mg | b. Preparation:

The active substance is screened, then carefully mixed with the mannitol and the microcrystalline cellulose by means of a planet-mixer. In order to obtain a product which can be granulated, the mixture is moistened with a 20% solution of polyvidone in methanol then, if necessary, with methanol. The moistened product is granulated by means of an oscillating granulator provided with a grate, the meshes of which have a 3 mm opening. The granules are dried at 45° C. in a ventilated oven, then the dried granules are screened by means of a sieve, the meshes of which have a 1 mm opening. The other ingredients are then added and carefully mixed with the granules, for example by means of a planet-mixer. The granules thus treated are compressed by means of a reciprocating or rotary press. The compressed tablets are packed in pill-boxes provided with a polyethylene cap or in blisters.

Recipes in the form of gelatin-coated pills

The granules obtained as shown above may be put in gelatine capsules instead of being compressed. For example the granules corresponding to recipe B are put in gelatine capsules having the size No. 2, each gelatine capsule containing 200 mg of the composition. The gelatine capsules are packed in pill-boxes or blisters.

Recipes in the form of suppositories a. Composition:

| 2-Amino-6-trifluoromethoxy-benzothiazole | 10 mg |
|---|---|
| Semi-synthetic glycerides | 1990 mg | b. Preparation:

The semi-synthetic glycerides are melted by heating at 40° C. and the active substance, finely powdered (particle size less than 100 microns), is incorporated by stirring. The mixture is run in preformed alveoles made of polyvinyl chloride and let cool.

What is claimed is:

1. A medicament, particularly useful as an anticonvulsant, anxiolytic and hypnotic, which contains a pharmaceutically acceptable vehicle and, as active substance, 1 to 50 mg per unit dose of 2-amino-6-trifluoromethoxy-benzothiazole or a salt of this compound with a pharmaceutically acceptable acid.

2. A medicament according to claim 1 wherein the pharmaceutically acceptable acid is selected from the group consisting of hydrochloric, hydrobromic, sulfuric, nitric, phosphoric, methanesulfonic and ethanedisulfonic acids.

3. A medicament according to claim 1 in the form of a compressed tablet containing 10 mg to 50 mg of active substance.

4. A medicament according to claim 1 in the form of a gelatin-coated pill containing 25 mg of active substance.

5. A medicament according to claim 1 in the form of a suppository containing 10 mg of active substance.

6. A process for treating a human suffering from convulsions or anxiety which comprises orally administering to said human 5 to 250 mg per day of 2-amino-6-trifluoromethoxy-benzothiazole or a salt thereof with a pharmaceutically acceptable acid.

7. A process according to claim 6 wherein the pharmaceutically acceptable acid is selected from the group consisting of hydrochloric, hydrobromic, sulfuric, nitric, phosphoric, methanesulfonic and ethanedisulfonic acids.